(12) United States Patent
Lenz et al.

(10) Patent No.: US 9,233,002 B2
(45) Date of Patent: Jan. 12, 2016

(54) SYSTEMS AND METHODS FOR TENSIONING LIGAMENTS AND OTHER SOFT TISSUES

(71) Applicant: Smith & Nephew, Inc., Memphis, TN (US)

(72) Inventors: Nathaniel Milton Lenz, Germantown, TN (US); Zachary Christopher Wilkinson, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/948,581

(22) Filed: Jul. 23, 2013

(65) Prior Publication Data

US 2013/0317620 A1 Nov. 28, 2013

Related U.S. Application Data

(63) Continuation of application No. 13/084,717, filed on Apr. 12, 2011, now Pat. No. 8,496,704.

(60) Provisional application No. 61/323,732, filed on Apr. 13, 2010.

(51) Int. Cl.
*A61F 2/08* (2006.01)
*A61F 2/38* (2006.01)
(Continued)

(52) U.S. Cl.
CPC ............... *A61F 2/389* (2013.01); *A61F 2/0811* (2013.01); *A61B 2017/565* (2013.01);
(Continued)

(58) Field of Classification Search
USPC ........... 623/13.12–13.14, 20.15, 20.27, 20.32
See application file for complete search history.

(56) References Cited

U.S. PATENT DOCUMENTS 3,953,899 A 5/1976 Charnley
4,246,660 A * 1/1981 Wevers ...................... 623/13.13
(Continued)

FOREIGN PATENT DOCUMENTS

WO WO2009056836 A3 10/2009
WO WO2011130208 A3 3/2012

OTHER PUBLICATIONS

International Search Report and Written Opinion for International Application No. PCT/US2011/032031, mailed Dec. 26, 2011.

*Primary Examiner* — David H Willse
*Assistant Examiner* — Javier Blanco
(74) *Attorney, Agent, or Firm* — Fish & Richardson P.C.

(57) ABSTRACT

Systems, methods and devices for tensioning posterior crucial ligaments during cruciate or bi-cruciate ligament-sparing arthroplasty. Non-limiting examples of such systems may include at least one series of tibial inserts of equal size; the at least one series of tibial inserts having at least one set of tibial inserts of equal thickness. The at least one set of tibial inserts of equal thickness may include at least two tibial inserts having different geometries in a posterior portion, the different geometries being configured to change the tension in the posterior cruciate ligament (PCL). The different geometries in the posterior portions of the tibial inserts are configured so as to allow the posterior cruciate ligament to be tensioned or loosened independently of the tibial insert thickness and/or size. By providing different posterior geometries for each insert within a set of a series, a surgeon may be provided with more flexibility in choosing an insert that satisfies stability requirements in a non-invasive manner.

1 Claim, 12 Drawing Sheets

(51) Int. Cl.
 *A61B 17/56* (2006.01)
 *A61F 2/30* (2006.01)
(52) U.S. Cl.
 CPC  *A61F 2002/0829* (2013.01); *A61F 2002/0852* (2013.01); *A61F 2002/0888* (2013.01); *A61F 2002/30462* (2013.01); *A61F 2002/30616* (2013.01); *A61F 2002/30688* (2013.01)

(56) References Cited

U.S. PATENT DOCUMENTS

| | | | |
|---|---|---|---|
| 4,340,978 A | 7/1982 | Buechel et al. | |
| 5,047,057 A | 9/1991 | Lawes | |
| 5,458,645 A | 10/1995 | Bertin | |
| 5,733,292 A | 3/1998 | Gustilo et al. | |
| 5,735,904 A | 4/1998 | Pappas | |
| 7,527,650 B2 | 5/2009 | Johnson et al. | |
| 7,578,821 B2 | 8/2009 | Fisher et al. | |
| 8,343,227 B2 | 1/2013 | Metzger et al. | |
| 2005/0187635 A1* | 8/2005 | Metzger | 623/20.15 |
| 2007/0185498 A2 | 8/2007 | Lavallee | |
| 2009/0222089 A1 | 9/2009 | Hauri et al. | |
| 2009/0240169 A1 | 9/2009 | Warkentine et al. | |
| 2010/0305698 A1 | 12/2010 | Metzger et al. | |
| 2010/0305709 A1 | 12/2010 | Metzger et al. | |
| 2011/0015749 A1 | 1/2011 | Engh et al. | |
| 2011/0022179 A1 | 1/2011 | Andriacchi et al. | |
| 2011/0029091 A1 | 2/2011 | Bojarski et al. | |
| 2011/0087332 A1 | 4/2011 | Bojarski et al. | |
| 2012/0078262 A1 | 3/2012 | Pinczewski et al. | |

* cited by examiner

SYSTEMS AND METHODS FOR TENSIONING LIGAMENTS AND OTHER SOFT TISSUES

CROSS-REFERENCE TO RELATED APPLICATIONS

This application is a continuation of U.S. patent application Ser. No. 13/084,717, filed Apr. 12, 2011, titled "SYSTEMS AND METHODS FOR TENSIONING LIGAMENTS AND OTHER SOFT TISSUES," now U.S. Pat. No. 8,496,704, which claims the benefit of U.S. Provisional Application Ser. No. 61/323,732, filed Apr. 13, 2010 titled "SYSTEM AND METHOD FOR TENSIONING CRUCIATE LIGAMENTS," the entire contents of which are hereby incorporated by reference.

BACKGROUND

1. Related Fields

Artificial body members used in knee and other joint arthroplasty, and systems and methods using the same, for tensioning ligaments, tendons or other soft tissues.

2. Related Art

There are currently three total knee arthroplasty (TKA) cruciate ligament options available to surgeons. A first option is to sacrifice both the posterior cruciate ligament (PCL) and the anterior cruciate ligament (ACL). A second option is to retain the PCL and sacrifice the ACL. A third option is to preserve both cruciate ligaments. Generally, the first and second options are more common, because most patients having indications for total knee arthroplasty also typically have an ACL deficiency. For younger and more active patients with a healthy posterior cruciate ligament, it may be desirable in some instances to select the second or third option and retain at least the PCL. In doing so, stability may in some cases be achieved with the patient's own ligamentous soft tissue, instead of the implant.

Referring now to FIGS. 1, 2A, and 2B, there are typically two approaches to retaining the PCL during total knee arthroplasty. To this end, surgeons may resect the entire proximal portion of the affected tibia (10) as shown in FIG. 2A, or may resect most portions of the proximal tibia, leaving only a small area (12) of protruding bone and cartilage (13, 15, 17) at the posterior portion as shown in FIGS. 1 and 2B. Because the PCL (20) has an attachment point (16) that is slightly inferior to the resection plane (14), the PCL (20) usually stays attached to the tibia (10) regardless of which method is used. The benefits and disadvantages for each of the PCL-sparing resection techniques shown in FIGS. 2A and 2B have been widely debated. It has been suggested by those in the art that the function of the PCL changes with removal of the bone above the PCL attachment to the tibia.

Many surgeons find it difficult to leave a small area (12) of protruding bone and cartilage (13, 15, 17) at the posterior portion of a proximal tibia (10) due to the location of the PCL and surrounding bony structure. In fact, many surgeons prefer a total proximal resection (14) because it takes less practice and decreases operating time. In addition, it is generally very easy to notch the small area (12) of remaining bone or accidentally cut it off. Therefore, the approach of many surgeons is to resect the entire proximal tibia (10) in the first place as shown in FIG. 2A.

The problem associated with the PCL-sparing technique of resecting the entire proximal tibia as shown in FIG. 2A is that it may affect laxity, stiffness, tension, and other kinematic factors of the PCL (20). Essentially, by removing the small area (12) of protruding bone and cartilage (13, 15, 17), the tension (T) in the PCL may be reduced and forces associated with the PCL may be altered. Additionally, some of the edges of the PCL (20) may be inadvertently cut along the resection plane (14), thereby increasing elasticity of the PCL due to a smaller diameter. A loose PCL may affect anterior-posterior stability of the femur in relationship to the tibia (10) and may defeat the purpose of retaining the PCL in the first place.

Another problem associated with some PCL-sparing techniques involving resecting the entire proximal tibia occurs during trial reduction. Tibial inserts of the patient's size and having different thicknesses are typically placed between the femur and tibia until the best possible stability throughout a full range of motion is achieved. Unfortunately, an appropriately sized insert may over-stretch the PCL, or under-stretch the PCL, leaving the surgeon to make compromises. Often, if the PCL is over-stretched or placed in too much tension after an appropriate insert thickness is selected, invasive and difficult soft tissue and ligament releasing is performed. Alternatively, if the PCL is too loose, under-stretched, or insufficient for stability, a deep dish cruciate-retaining insert or a posterior stabilized implant may be used.

SUMMARY

According to one embodiment of the invention, there may be provided a system for tensioning posterior cruciate ligaments during cruciate or bi-cruciate ligament-sparing arthroplasty. The system includes at least one series of tibial inserts of equal size; the at least one series of tibial inserts having at least one set of tibial inserts of equal thickness. The at least one set of tibial inserts of equal thickness may include at least two tibial inserts having different geometries in a posterior portion, the different geometries being configured to change the tension in the posterior cruciate ligament (PCL). The different geometries in the posterior portions of the tibial inserts are configured so as to allow the posterior cruciate ligament to be tensioned or loosened independently of the tibial insert thickness and/or size. By providing different posterior geometries for each insert within a set of a series, a surgeon may be provided with more flexibility in choosing an insert that satisfies stability requirements in a non-invasive manner.

According to one embodiment of the invention, there may be provided a kit for tensioning posterior cruciate ligaments during cruciate or bi-cruciate ligament-sparing arthroplasty. The kit contains at least one series of tibial inserts of equal size; the at least one series of tibial inserts comprising at least one set of tibial inserts of equal thickness. The at least one set of tibial inserts of equal thickness may include at least two tibial inserts having different geometries in a posterior portion, the different geometries being configured to change the tension in the posterior cruciate ligament (PCL). The different geometries in the posterior portions of the tibial inserts are configured so as to allow the posterior cruciate ligament to be tensioned or loosened independently of the tibial insert thickness and/or size. By providing different posterior geometries for each insert within a set of a series, a surgeon may be provided with more flexibility in choosing an insert that satisfies stability requirements in a non-invasive manner.

According to another embodiment, there may be provided a method of using such systems.

In some embodiments, surgeons may extract the benefit of leaving the small area (12) of protruding bone and cartilage (13, 15, 17), with the comfort and ease of a full proximal tibial resection (14), no ligamentous releases, and no need to change articular geometries.

In some embodiments, the surgeon is provided with the option to vary the tension in the PCL with different tibial insert options. In some embodiments, a kit allows the surgeon to vary the tension in the PCL independently of the size and thickness of the tibial insert to achieve an optimal fit, function, and stability for the patient while simultaneously eliminating or minimizing the need for invasive soft tissue releases. Some embodiments further provide a method of using such a system and kit.

In some embodiments, there is provided a system of components for facilitating a knee arthroplasty procedure, the system of components comprising a first series of knee arthroplasty components including at least a first knee arthroplasty component and a second knee arthroplasty component, wherein the first and second knee arthroplasty components are of equal size; a second series of knee arthroplasty components including at least a third knee arthroplasty component and a fourth knee arthroplasty component, wherein the third and fourth knee arthroplasty components are of equal size, and wherein the first and second knee arthroplasty components are not of equal size with the third and fourth knee arthroplasty components; wherein each of the first, second, third and fourth knee arthroplasty components includes a wrapping surface configured for wrapping contact with a posterior cruciate ligament; wherein a geometry of the wrapping surface of the first knee arthroplasty component is different from a geometry of the wrapping surface of the second knee arthroplasty component such that the wrapping surface of the first knee arthroplasty component is configured to generate at least one of a different tension in or direction of force on the posterior cruciate ligament relative to the wrapping surface of the second knee arthroplasty component; and wherein a geometry of the wrapping surface of the third knee arthroplasty component is different from a geometry of the wrapping surface of the fourth knee arthroplasty component such that the wrapping surface of the third knee arthroplasty component is configured to generate at least one of a different tension in or direction of force on the posterior cruciate ligament relative to the wrapping surface of the fourth knee arthroplasty component.

In some embodiments, the first knee arthroplasty component has an overall thickness that is the same as the second knee arthroplasty component and the third knee arthroplasty component has an overall thickness that is the same as the fourth knee arthroplasty component.

In some embodiments, the first series further comprises a fifth knee arthroplasty component, wherein the fifth knee arthroplasty component has an overall thickness that is different from the overall thickness of the first and second knee arthroplasty components; and the second series further comprises a sixth knee arthroplasty component, wherein the sixth knee arthroplasty component has an overall thickness that is different from the overall thickness of the third and fourth knee arthroplasty components.

In some embodiments, the first, second, third and fourth knee arthroplasty components are tibial components and the wrapping surfaces are notches formed in posterior edges of the knee arthroplasty components.

In some embodiments, the notches are centrally located between medial and lateral condylar articulating surfaces.

In some embodiments, the tibial components are tibial inserts.

In some embodiments, the tibial inserts are tibial trials.

In some embodiments, the tibial inserts are cruciate sparing tibial inserts.

In some embodiments, each of the knee arthroplasty components include an anterior-posterior axis and the wrapping surface of the first knee arthroplasty component is positioned further posteriorily along the anterior-posterior axis of the first knee arthroplasty component relative to the wrapping surface of the second knee arthroplasty component.

In some embodiments, each of the knee arthroplasty components include an anterior-posterior axis and the wrapping surface of the first knee arthroplasty component is oriented at a different angle to the anterior-posterior axis of the first knee arthroplasty component relative to the wrapping surface of the second knee arthroplasty component.

In some embodiments, the first knee arthroplasty component is positioned further posteriorily along the anterior-posterior axis of the first knee arthroplasty component relative to the wrapping surface of the second knee arthroplasty component.

In some embodiments, the wrapping surfaces are bowed inwardly.

In some embodiments, the wrapping surface of the first knee arthroplasty component extends further superiorly relative to the wrapping surface of the second knee arthroplasty component.

In some embodiments, the knee arthroplasty components include an anterior-posterior axis and the wrapping surface of the first knee arthroplasty component is positioned further posteriorily along the anterior-posterior axis of the first knee arthroplasty component relative to the wrapping surface of the second knee arthroplasty component; and the wrapping surface of the first knee arthroplasty component extends further superiorly relative to the wrapping surface of the second knee arthroplasty component.

In some embodiments, the first and second series of knee arthroplasty components are part of a kit of knee arthroplasty components.

In some embodiments, there is provided a system of components for facilitating a knee arthroplasty procedure, the system of components comprising: a first series of knee arthroplasty components including at least a first knee arthroplasty component and a second knee arthroplasty component, wherein the first and second knee arthroplasty components are of equal size; a second series of knee arthroplasty components including at least a third knee arthroplasty component and a fourth knee arthroplasty component, wherein the third and fourth knee arthroplasty components are of equal size, and wherein the first and second knee arthroplasty components are not of equal size with the third and fourth knee arthroplasty components; wherein each of the first, second, third and fourth knee arthroplasty components includes a wrapping surface configured for wrapping contact with a posterior cruciate ligament; wherein a geometry of the wrapping surface of the first knee arthroplasty component is different from a geometry of the wrapping surface of the second knee arthroplasty component such that the wrapping surface of the first knee arthroplasty component is configured to generate at least one of a different tension in or direction of force on the posterior cruciate ligament relative to the wrapping surface of the second knee arthroplasty component; wherein a geometry of the wrapping surface of the third knee arthroplasty component is different from a geometry of the wrapping surface of the fourth knee arthroplasty component such that the wrapping surface of the third knee arthroplasty component is configured to generate at least one of a different tension in or direction of force on the posterior cruciate ligament relative to the wrapping surface of the fourth knee arthroplasty component; wherein the first knee arthroplasty component has an overall thickness that is the same as the second knee arthroplasty component and the third knee arthroplasty component has an overall thickness that is the same as the fourth knee arthroplasty component; and wherein the first, second, third and fourth knee arthroplasty components are tibial components and the wrapping surfaces are formed proximate posterior edges of the knee arthroplasty components.

In some embodiments, there is provided a method for performing a joint arthroplasty procedure on a joint, comprising: determining a desired size for an implant for the joint; positioning a first implant of the desired size relative to the joint such that a soft tissue associated with the joint is in wrapping contact with a first wrapping surface of the first implant; assessing the joint while the first implant is positioned relative to the joint and the soft tissue is in wrapping contact with the first wrapping surface; positioning a second wrapping surface in wrapping contact with the soft tissue; assessing the joint while the soft tissue is in wrapping contact with the second wrapping surface; and implanting a final joint implant in the joint.

In some embodiments, positioning the second wrapping surface in wrapping contact with the soft tissue comprises positioning a second implant of the same desired size relative to the joint such that the soft tissue associated with the joint is in wrapping contact with the second wrapping surface of the second implant.

In some embodiments, positioning the first implant comprises positioning the first implant such that a posterior cruciate ligament is in wrapping contact with a notch in a posterior edge of a first tibial implant such that the posterior cruciate ligament is tensioned at a first tension or subjected to a first force direction.

In some embodiments, positioning the second implant comprises positioning the second implant such that the posterior cruciate ligament is in wrapping contact with a notch in a posterior edge of a second tibial implant such that the posterior cruciate ligament is tensioned at a different tension or subjected to a different force direction.

In some embodiments, positioning the second wrapping surface in wrapping contact with the soft tissue comprises adjusting or modifying the first implant.

In some embodiments, there is provided a kit of joint arthroplasty components, comprising: a plurality of size series of components, each size series of components comprising a plurality of components of equal size in a transverse plane; wherein each size series of components further comprises a plurality of thickness sets of components, each thickness set of components comprising a plurality of components of equal thickness in a sagittal plane; and wherein each thickness set of components further comprises a plurality of soft tissue accommodation components, wherein each soft tissue accommodation component comprises a different soft tissue accommodation geometry.

In some embodiments, each thickness set of components comprises a plurality of components having the same articular configuration.

Further areas of applicability of the invention will become apparent from the detailed description provided hereinafter. It should be understood that the detailed description and specific examples, while indicating certain embodiments of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION OF THE DRAWINGS

The following description of the drawings is merely exemplary in nature and is in no way intended to limit the invention, its application, or uses.

As discussed above, certain embodiments of the invention provide, in part, an orthopaedic system that facilitates a surgeon adjusting PCL tension independently of other tibial sizes, shapes, thickness, and other features. Such embodiments may further provide, in part, tibial inserts that use posterior geometry changes that can change the tension in a posterior-cruciate ligament and/or change the direction of the forces generated by or acting on the PCL to match an individual patient's needs or to optimize the performance of a given prosthesis. By selecting a tibial insert that has the most appropriate surface for the PCL to articulate with, independently of other tibial insert features and configurations, a surgeon is armed with more intraoperative options without the need for invasive soft tissue releases or other compromises.

In some, although not necessarily all, embodiments, it may be preferred that proper sizing and trial reduction be performed prior to utilizing the PCL-tension-adjusting tibial inserts of the invention; however, the method steps disclosed herein may be practiced in any order, alone, or in combination with other method steps.

The usefulness of the present invention is not limited to tibial inserts, but may also, for instance and without limitation, have similar applicability with femoral components in a similar manner as would be appreciated by those of ordinary skill in the art. For instance, similar geometry changes on a femoral component adjacent the femoral PCL attachment location may serve to adjust tension in the PCL as well as change the direction of the forces exerted on and by the PCL. Such geometry changes can be implemented by an integrally-formed shape, or, a separate add-on device that is fixed to the femoral component and which may be adjustable to "tune" the tension in the PCL and/or the direction of the forces generated by or acting on the PCL. In still other embodiments, the concepts, structures, systems and methods of the embodiments described herein may be applied to other ligaments, tendons or other soft tissues of the knee or other joints connected by such soft tissues.

Figure 1:
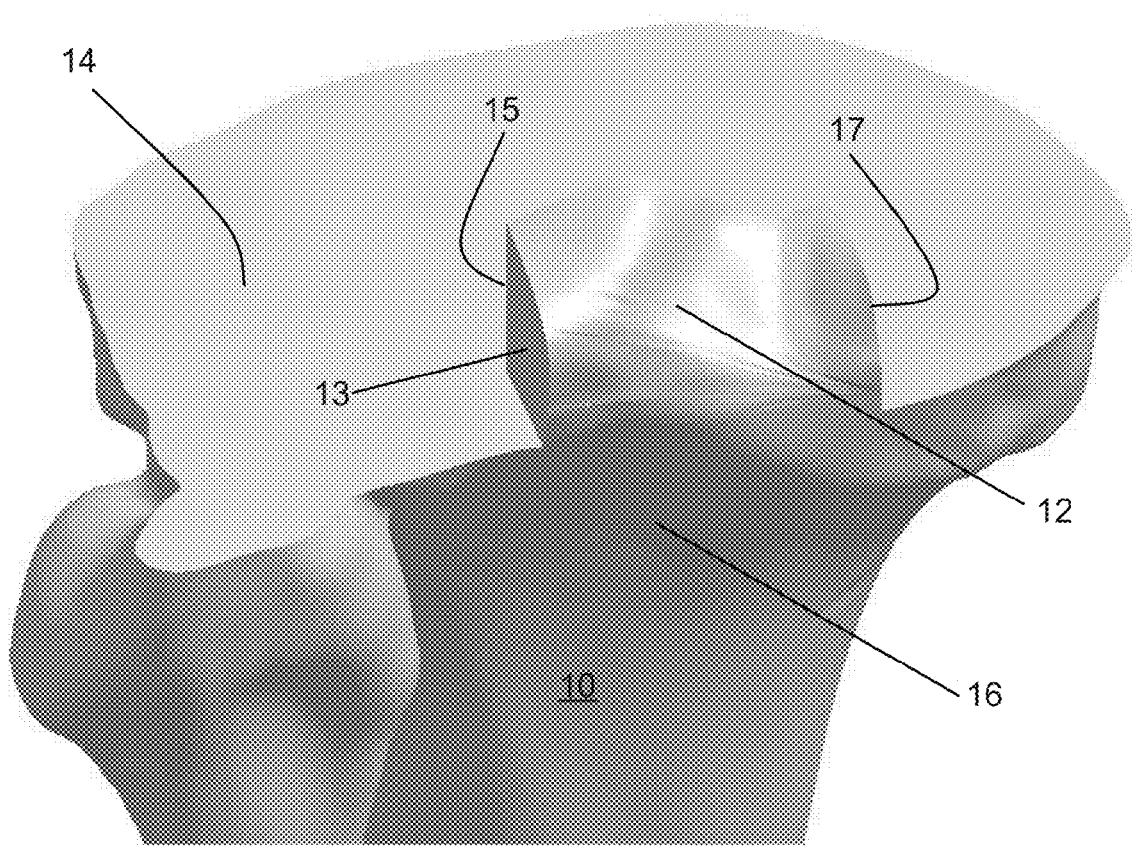
FIG. 1 is a posterolateral view of a proximal tibia after a first conventional PCL-sparing resection.
Figure 2A:
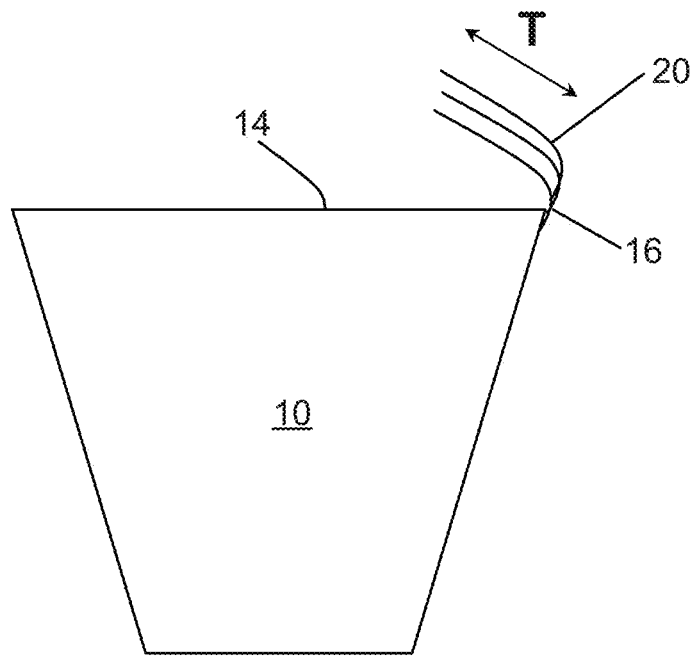
FIG. 2A is a side (sagittal) schematic representation of a proximal tibia after a second conventional PCL-sparing resection.
Figure 2B:
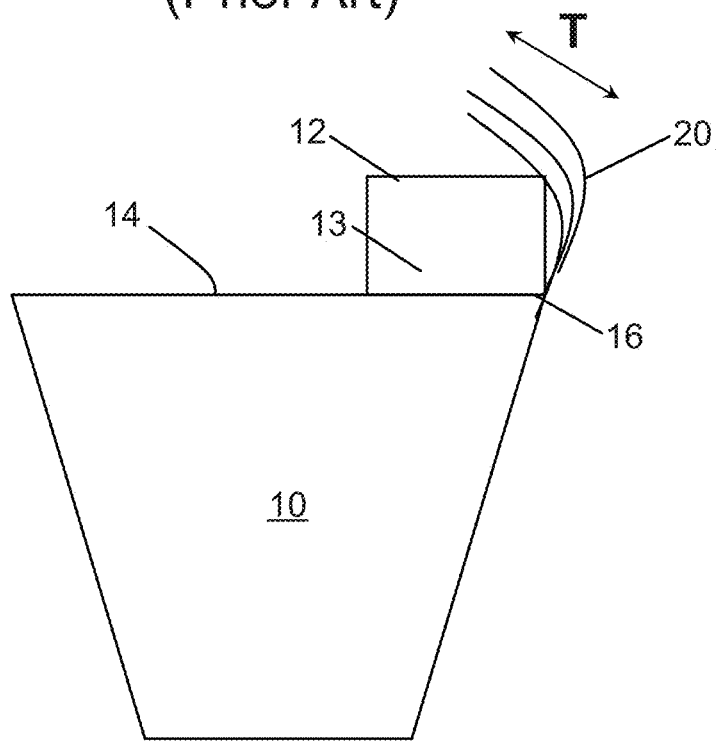
FIG. 2B is a side (sagittal) schematic representation of the first conventional PCL-sparing resection shown in FIG. 1.

As previously stated above, FIGS. 1, 2A, and 2B illustrate conventional approaches to retaining the PCL during total knee arthroplasty. To this end, surgeons have the option to resect the entire proximal portion of the affected tibia (10) as shown in FIG. 2A or may resect most portions of the proximal tibia, leaving only a small area (12) of protruding bone and cartilage (13, 15, 17) at the posterior portion as shown in FIGS. 1 and 2B. Because the PCL (20) has an attachment point (16) that is slightly inferior to the resection plane (14), the PCL (20) stays attached to the tibia (10) regardless of which method is used.

Figure 3:
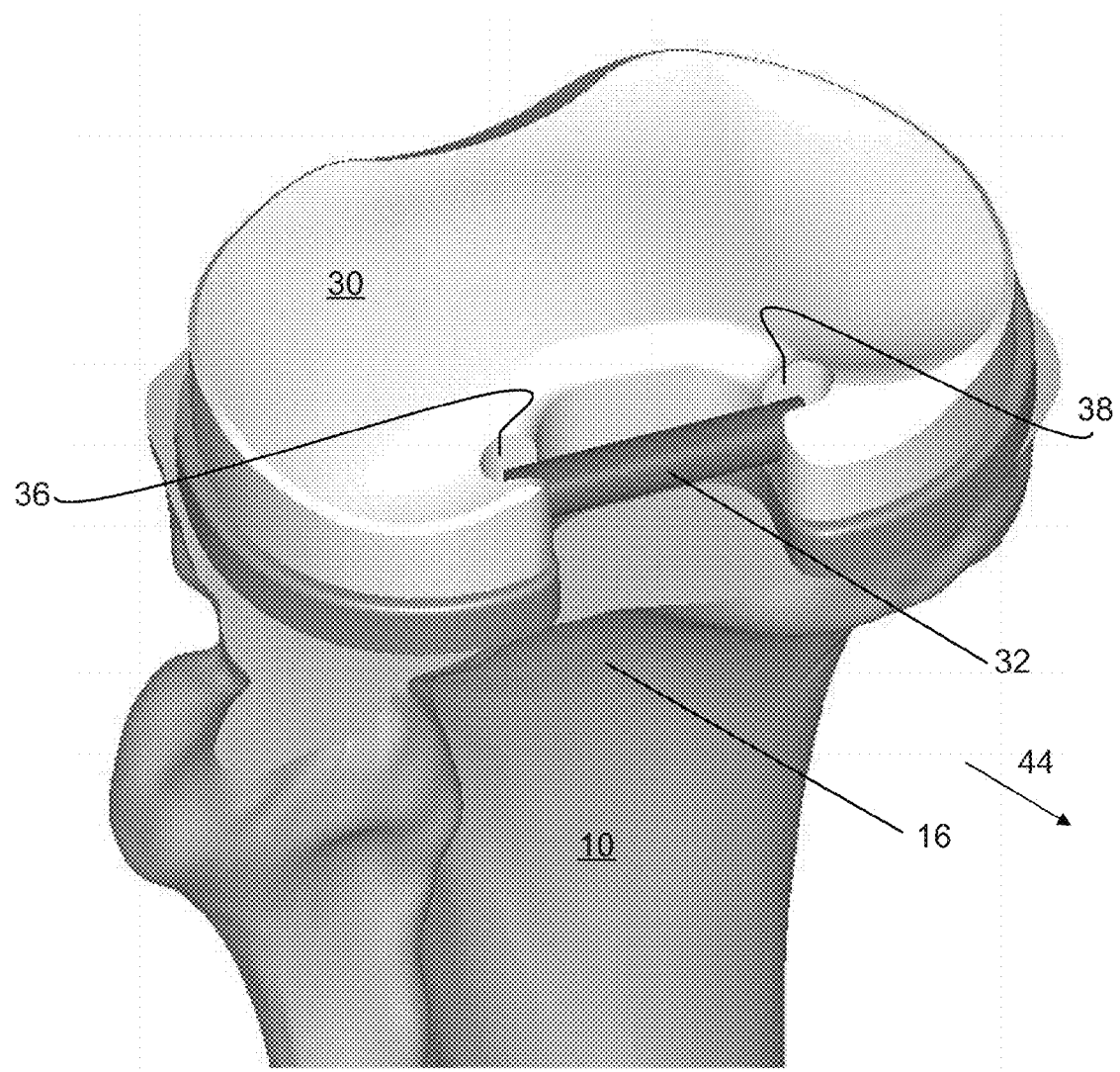
FIG. 3 is a posterolateral view of a proximal tibia incorporating one embodiment of a tibial insert.

FIG. 3 illustrates a posterolateral view of a proximal tibia (10) incorporating a tibial insert (30) according to some embodiments. The insert (30) includes a mechanism for tensioning a PCL (32), which, in this particular embodiment, is a removable pin. Other tensioning mechanisms may be removably attached or integrally-formed with a posterior (44) portion of the tibial insert (30). Such tensioning mechanisms (32) may be an adjustable tensioning device such as a turnbuckle, cam, jack mechanism, tensioning pin, or may simply comprise a series of interchangeable dowels having different cross-sectional geometries, sizes, cam surfaces, and/or shapes, and which can be selectively swapped out of the tibial insert (30). In the embodiment shown in FIG. 3, there is a holder (36,38) for holding the PCL tensioning mechanism (32), at least temporarily securing it to the insert (30). In other embodiments, other holding mechanisms may include, without limitation, any one or more of a hole, channel, track, groove, pocket, snap-fit mechanism (e.g., plastic barb or ball detent), press-fit, or other conventional or non-conventional devices as will be appreciated by those of ordinary skill in the art.

In the embodiment shown in FIG. 3, the tensioning mechanism (32) is a wrapping surface configured for wrapping contact with the PCL. In some embodiments, it may be desirable for the wrapping surface to be a polished or otherwise smooth surface, since the PCL will be partially wrapped around it and may articulate and/or experience other motions or micro-motions with respect to the wrapping surface. In some embodiments, the wrapping surface may be poly-ethylene, metal, ceramic, oxidized zirconium, cobalt chrome, or another material or other treatments of materials.

Figure 4A:
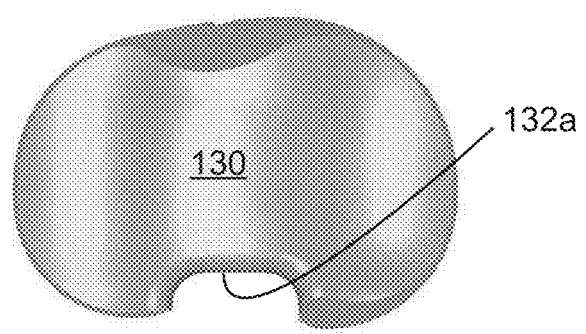
FIGS. 4A-4C. are top (superior) views of tibial inserts according to another embodiment.
Figure 4B:
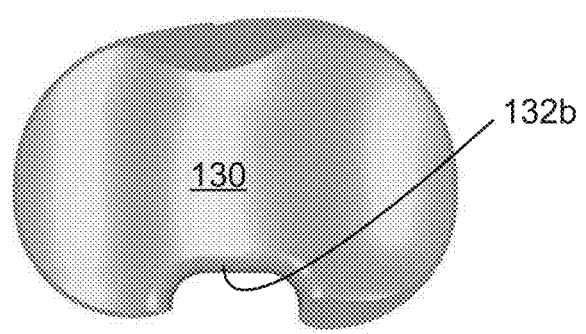
Figure 4C:
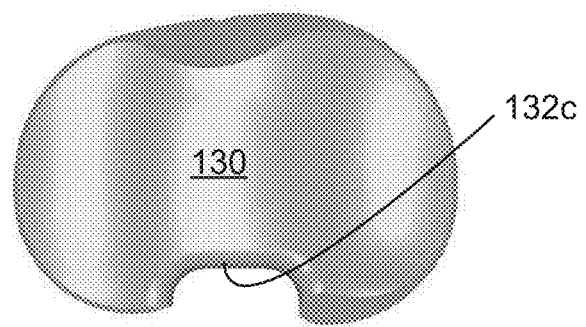

FIGS. 4A-4C illustrate a set of tibial inserts according to some embodiments. The set of tibial inserts (130) each have a similar size and thickness with the exception that a posterior geometry changes between the tibial inserts (130) in order to change the tension in the PCL. The change in geometry for the embodiment shown in FIGS. 4A-4C comprises a posterior wall (132a,132b,132c) that is generally perpendicular to the anterior-posterior axis and is generally located at different positions along the anterior-posterior axis for different tibial inserts (130) in the set. FIG. 4A illustrates a posterior wall (132a) that is positioned more anteriorly than either of the posterior walls (132b,132c) found in FIG. 4B or 4C. The insert (130) shown in FIG. 4C generally places a higher tension in the PCL than the inserts (130) shown in FIGS. 4A and 4B. The insert (130) shown in FIG. 4A generally places a lower tension in the PCL than the inserts (130) shown in FIGS. 4B and 4C. In this particular embodiment, portions of these posterior walls are wrapping surfaces/tensioning mechanisms.

Figure 5:
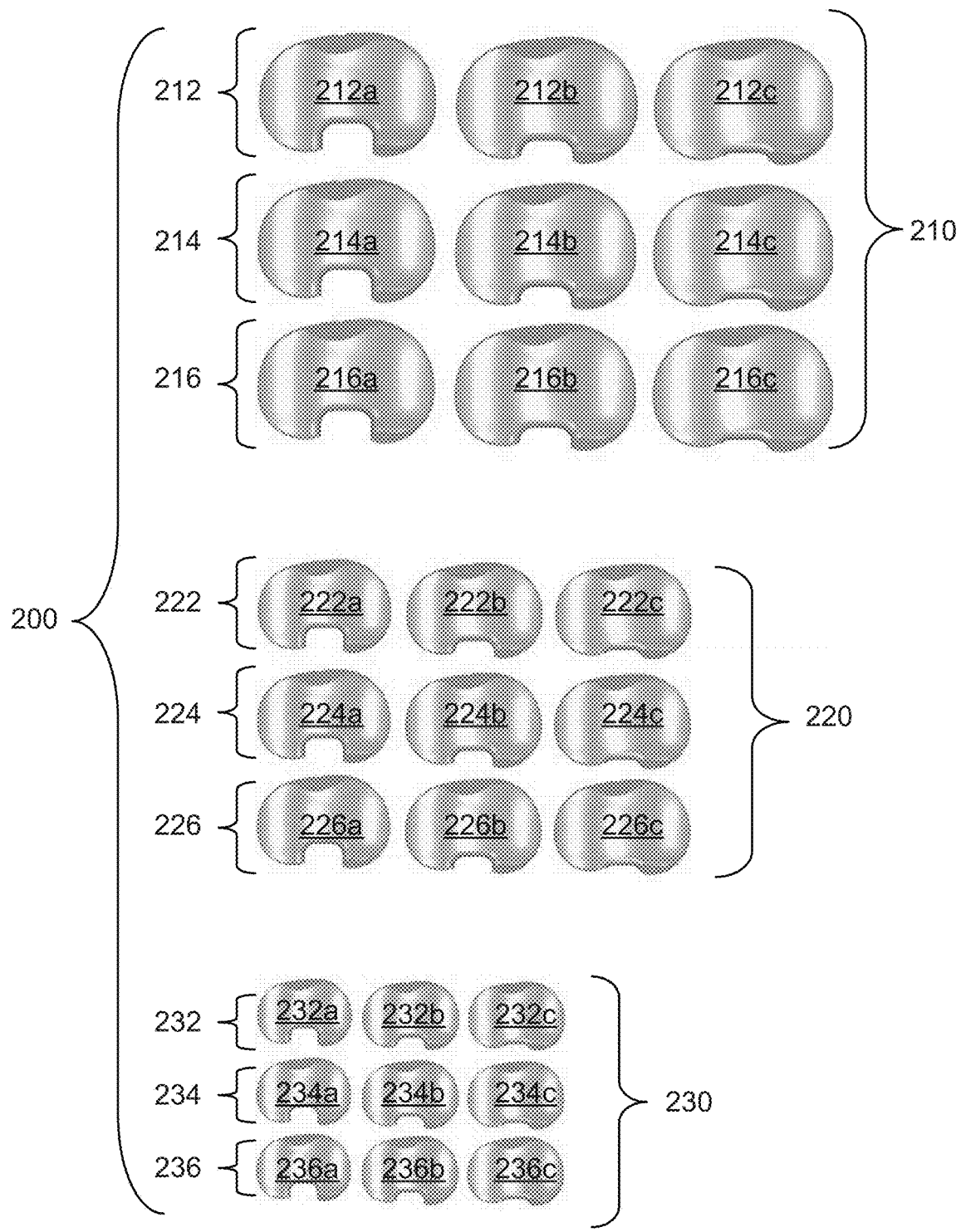
FIG. 5 illustrates a top (superior) view of a system according to some embodiments.

FIG. 5 illustrates a top (superior) view of a system (200) according to some embodiments. The system (200) includes three series (210,220,230) of tibial inserts of equal size. In other embodiments, other numbers of series may be present. Each of the one or more series (210,220,230) shown in FIG. 5 includes three sets (212,214,216; 222,224,226; 232,234, 236) (which may also vary in number) of tibial inserts having the same thickness and/or articular configuration (e.g., deep-dish). Each of the one or more sets (212,214,216; 222,224, 226; 232,234,236) shown in FIG. 5 includes three tibial inserts (which may also vary in number) having different posterior geometries, the different posterior geometries being adapted and configured to change at least one of or both the tension in the PCL and a direction of force exerted on or by the PCL (e.g. act as tensioning mechanisms/wrapping surfaces).

For example, without limitation, an orthopaedic system (200) may include a series (210) of size "X" tibial inserts. The patient is measured intra-operatively and is deemed to be a candidate for a size "X" tibial insert. The surgeon selects the size "X" series (210) of tibial inserts and begins trial reduction to optimize flexion gap. In order to do this, the surgeon selects one standard insert from each set (212,214,216) of inserts within the series (210). The surgeon selects the set (212,214,216) of inserts that provides the best general stability and flexion gap throughout full or partial range of motion. For instance, if set (214) yields the best stability for the size "X" patient and provides the optimum thickness for a tibial insert for the patient, then the surgeon begins a second trial reduction for PCL tension and stability using the set (214) of tibial inserts. Next, the surgeon assesses the tightness or laxity of the PCL throughout a range of motion and selects a tibial insert (214a,214b,214c) within the set (214) of tibial inserts that provides the best tension, stability, and/or positioning of the PCL for optimum stability when using a size "X" series (210) tibial insert having a thickness as defined by set (214), without the need for release of the PCL or surrounding soft or ligamentous tissue.

Figure 6:
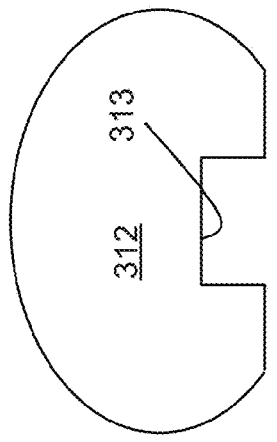
FIG. 6. illustrates a top (superior) view of a set of tibial inserts according to some embodiments.
Figure 6:
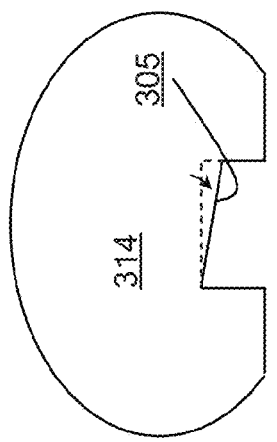
Figure 6:
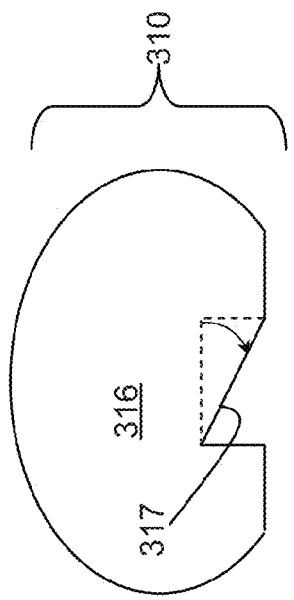

FIG. 6 illustrates a top (superior) view of a set of tibial inserts according to some embodiments. A first tibial insert (312) in the set includes a first posterior geometry that comprises a first posterior wall (313) at a first specified location along the anterior-posterior axis. A second tibial insert (314) in the set includes a second posterior geometry that comprises a second posterior wall (315) at a second specified location along the anterior-posterior axis which is more posterior than the first specified location. A third tibial insert (316) in the set includes a third posterior geometry that comprises a third posterior wall (317) at a third specified location along the anterior-posterior axis which is more posterior than both of the first and second specified locations. The first, second, and third posterior walls (313,315,317) are each positioned at different angles relative to the anterior-posterior axis. This allows the direction of imparted and reaction forces associated with the PCL to be changed between inserts, independently of the size, thickness, and articular configuration of the inserts (312,314,316). It also allows the PCL to be tensioned in different amounts between inserts, independently of the size, thickness, and articular configuration of the inserts (312, 314,316).

Figure 7:
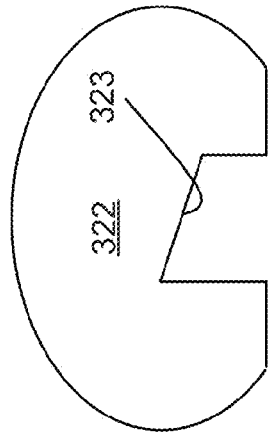
FIG. 7. illustrates a top (superior) view of a set of tibial inserts according to some embodiments.
Figure 7:
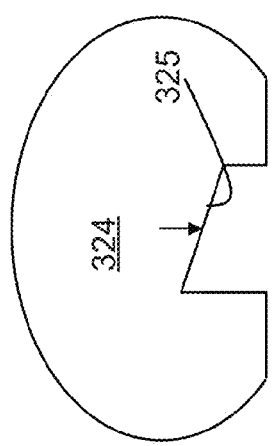
Figure 7:
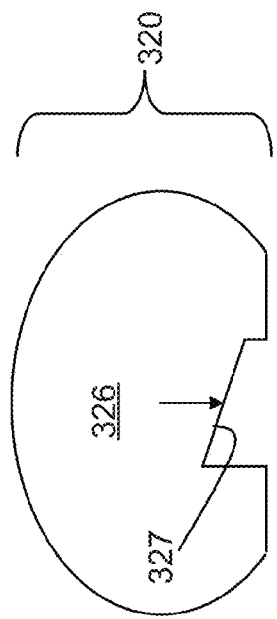

FIG. 7 illustrates a top (superior) view of a set of tibial inserts according to some embodiments. A first tibial insert (322) in the set includes a first posterior geometry that comprises a first posterior wall (323) at a first specified location along the anterior-posterior axis. A second tibial insert (324) in the set includes a second posterior geometry that comprises a second posterior wall (325) at a second specified location along the anterior-posterior axis which is more posterior than the first specified location. A third tibial insert (326) in the set includes a third posterior geometry that comprises a third posterior wall (327) at a third specified location along the anterior-posterior axis which is more posterior than both of the first and second specified locations. The first, second, and third posterior walls (323,325,327) are each positioned at the same angle relative to the anterior-posterior axis. This allows the PCL to be tensioned in different amounts between inserts, independently of the size, thickness, and articular configuration of the inserts (322,324,326), while still maintaining the direction of all imparted and reaction forces associated with the PCL.

Figure 8:
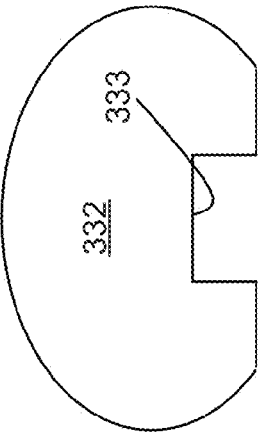
FIG. 8. illustrates a top (superior) view of a set of tibial inserts according to some embodiments.
Figure 8:
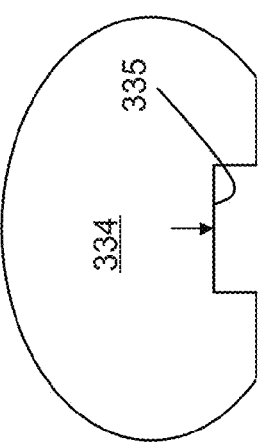
Figure 8:
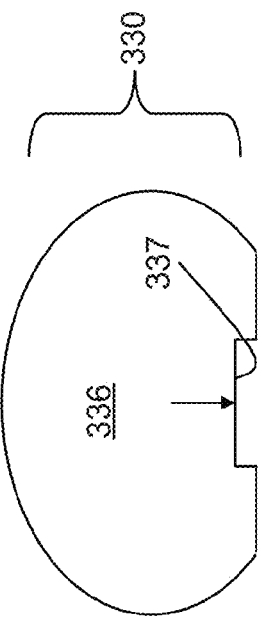

FIG. 8 illustrates a top (superior) view of a set of tibial inserts according to some embodiments. A first tibial insert (332) in the set includes a first posterior geometry that comprises a first posterior wall (333) at a first specified location along the anterior-posterior axis. A second tibial insert (334) in the set includes a second posterior geometry that comprises a second posterior wall (335) at a second specified location along the anterior-posterior axis which is more posterior than the first specified location. A third tibial insert (336) in the set includes a third posterior geometry that comprises a third posterior wall (337) at a third specified location along the anterior-posterior axis which is more posterior than both of the first and second specified locations. The first, second, and third posterior walls (333,335,337) are each positioned at the same angle relative to the anterior-posterior axis, and are each generally positioned orthogonal to the anterior-posterior axis. This allows the PCL to be tensioned in different amounts between inserts, independently of the size, thickness, and articular configuration of the inserts (332,334,336), while still maintaining the direction of all imparted and reaction forces associated with the PCL.

Figure 9:
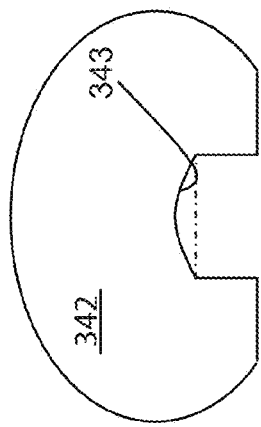
FIG. 9. illustrates a top (superior) view of a set of tibial inserts according to some embodiments.
Figure 9:
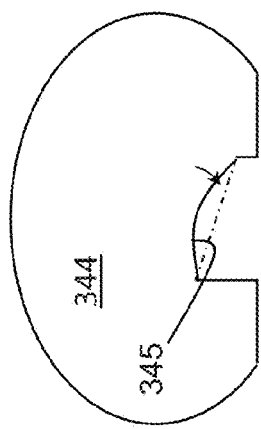
Figure 9:
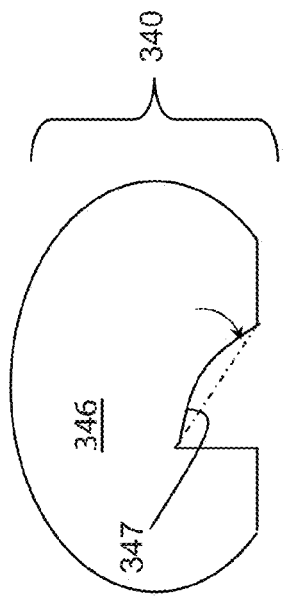

FIG. 9 illustrates a top (superior) view of a set of tibial inserts according to some embodiments. Similar to FIG. 6, FIG. 9 shows a first tibial insert (342) in the set that includes a first posterior geometry having a first posterior wall (343) at a first specified location along the anterior-posterior axis. A second tibial insert (344) in the set includes a second posterior geometry that comprises a second posterior wall (345) at a second specified location along the anterior-posterior axis which is more posterior than the first specified location. A third tibial insert (346) in the set includes a third posterior geometry that comprises a third posterior wall (347) at a third specified location along the anterior-posterior axis which is more posterior than both of the first and second specified locations. The first, second, and third posterior walls (343, 345,347) are each positioned at different angles relative to the anterior-posterior axis. This allows the direction of all imparted and reaction forces associated with the PCL to be changed between inserts, independently of the size, thickness, and articular configuration of the inserts (342,344,346). It also allows the PCL to be tensioned in different amounts between inserts, independently of the size, thickness, and articular configuration of the inserts (342,344,346).

Because the first, second and third posterior walls (343, 345,347) are angled to change the direction of imparted and reaction forces associated with the PCL, as well as the PCL tension, the walls (343,345,347) may be bowed or be provided with a concavity in order to keep the PCL centered within the posterior walls (343,345,347), and/or to keep the PCL from sliding medially or laterally out of the vicinity of the posterior walls (343,345,347).

Figure 10:
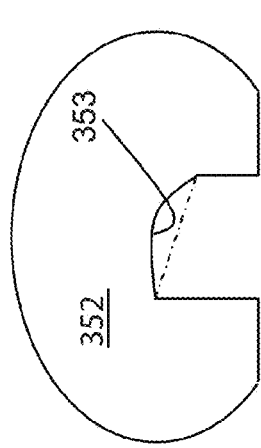
FIG. 10. illustrates a top (superior) view of a set of tibial inserts according to some embodiments.
Figure 10:
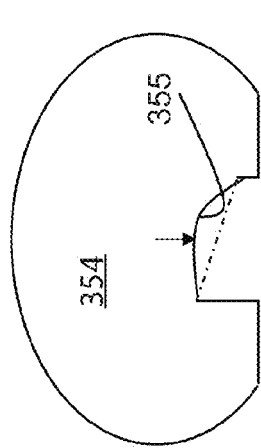
Figure 10:
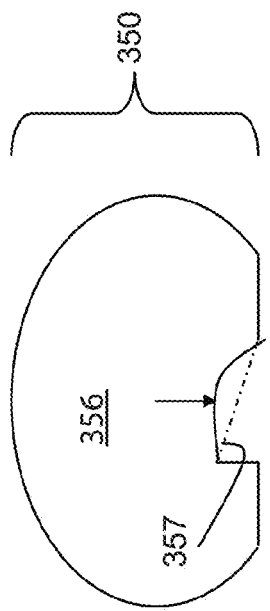

FIG. 10 illustrates a top (superior) view of a set of tibial inserts according to some embodiments. A first tibial insert (352) in the set includes a first posterior geometry including a first posterior wall (353) at a first specified location along the anterior-posterior axis. A second tibial insert (354) in the set includes a second posterior geometry including a second posterior wall (355) at a second specified location along the anterior-posterior axis, which is more posterior than the first specified location. A third tibial insert (356) in the set includes a third posterior geometry having a third posterior wall (357) at a third specified location along the anterior-posterior axis, which is more posterior than both of the first and second specified locations. The first, second, and third posterior walls (353,355,357) are each positioned at the same angle relative to the anterior-posterior axis. This allows the PCL to be tensioned in different amounts between inserts, independently of the size, thickness, and articular configuration of the inserts (352,354,356), while still maintaining the direction of imparted and reaction forces associated with the PCL.

Because the first, second and third posterior walls (353, 355,357) are angled, the walls (353,355,357) may be bowed or be provided with a concavity in order to keep the PCL centered within the posterior walls (353,355,357), and/or to keep the PCL from sliding medially or laterally out of the vicinity of the posterior walls (353,355,357).

Figure 11:
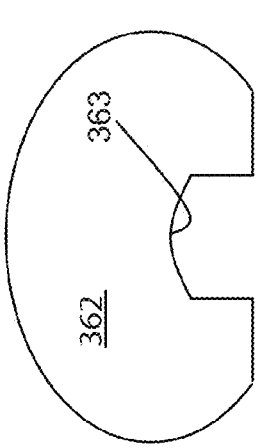
FIG. 11. illustrates a top (superior) view of a set of tibial inserts according to some embodiments.
Figure 11:
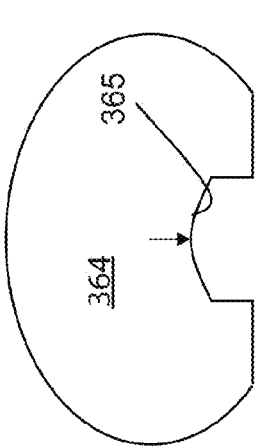
Figure 11:
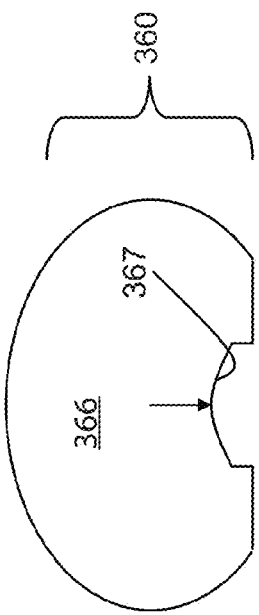

FIG. 11 illustrates a top (superior) view of a set of tibial inserts according to some embodiments. A first tibial insert (362) in the set includes a first posterior geometry having a first posterior wall (363) at a first specified location along the anterior-posterior axis. A second tibial insert (364) in the set includes a second posterior geometry having a second posterior wall (365) at a second specified location along the anterior-posterior axis which is more posterior than the first specified location. A third tibial insert (366) in the set includes a third posterior geometry having a third posterior wall (367) at a third specified location along the anterior-posterior axis, which is more posterior than both of the first and second specified locations. The first, second, and third posterior walls (363,365,367) are each positioned at the same angle relative to the anterior-posterior axis and are each generally positioned orthogonal to the anterior-posterior axis. This allows the PCL to be tensioned in different amounts between inserts, independently of the size, thickness, and articular configuration of the inserts (362,364,366), while still maintaining the direction of imparted and reaction forces associated with the PCL. In order to keep the PCL centered within the posterior walls (363,365,367) and/or to keep the PCL from sliding medially or laterally out of the vicinity of the posterior walls (363,365,367), the first, second and third posterior walls (363, 365,367) may be bowed or be provided with a concavity as illustrated.

Figure 12:
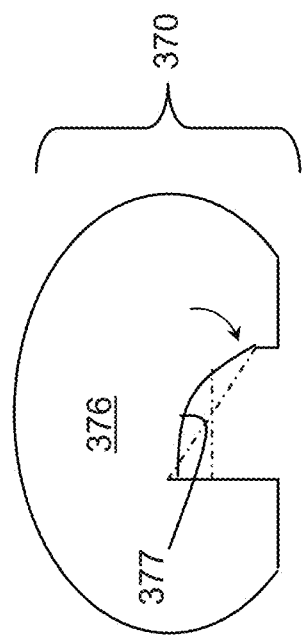
FIG. 12. illustrates a top (superior) view of a set of tibial inserts according to some embodiments.
Figure 12:
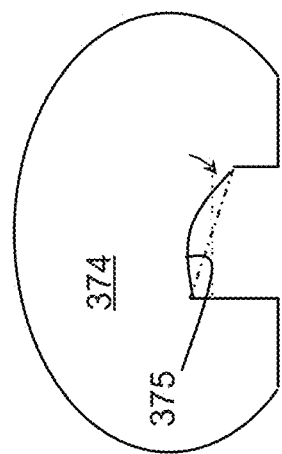
Figure 12:
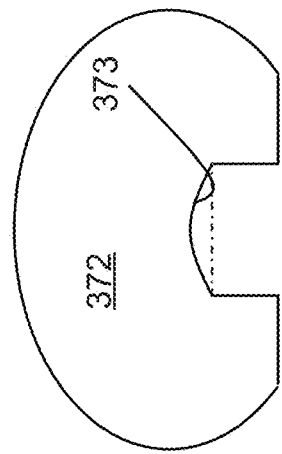

FIG. 12 illustrates a top (superior) view of a set of tibial inserts according to some embodiments. FIG. 12 is similar to FIG. 9, in that the angle of the posterior walls (373,375,377)

changes to change the direction of imparted and reaction forces associated with the PCL between inserts, independently of the size, thickness, and articular configuration of the inserts (372,374,376). However, the centroid of posterior walls (373,375,377) of the tibial inserts (372,374,376) shown in FIG. 12 do not move posteriorly between inserts. In doing so, while the direction of imparted and reaction forces associated with the PCL changes between inserts, independently of the size, thickness, and articular configuration of the inserts (372,374,376), the tension in the PCL does not necessarily change between inserts, or at least change to as great of an extent as if the centroid of the posterior wall was moved anterior or posterior.

Because the first, second and third posterior walls (373, 375,377) are angled, the walls (373,375,377) may be bowed or be provided with a concavity as shown, in order to keep the PCL centered within the posterior walls (373,375,377), and/or to keep the PCL from sliding medially or laterally out of the vicinity of the posterior walls (373,375,377).

Figure 13:
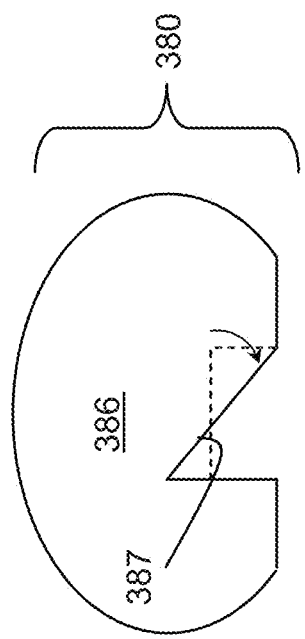
FIG. 13. illustrates a top (superior) view of a set of tibial inserts according to some embodiments.
Figure 13:
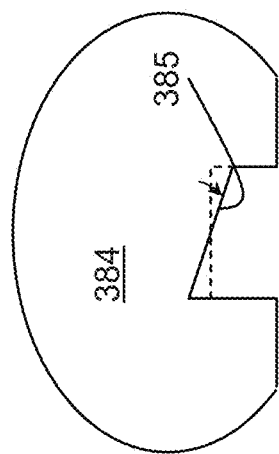
Figure 13:
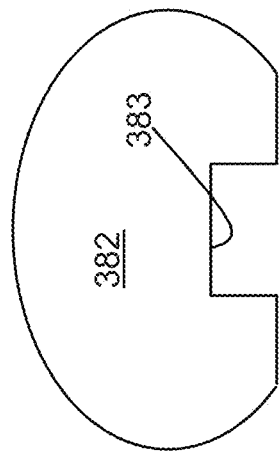

FIG. 13. illustrates a top (superior) view of a set of tibial inserts according to some embodiments. FIG. 13 essentially illustrates a similar embodiment to the one shown in FIG. 12, but having posterior walls (383,385,387) with more extreme angle inclinations and no concavities.

Figure 14:
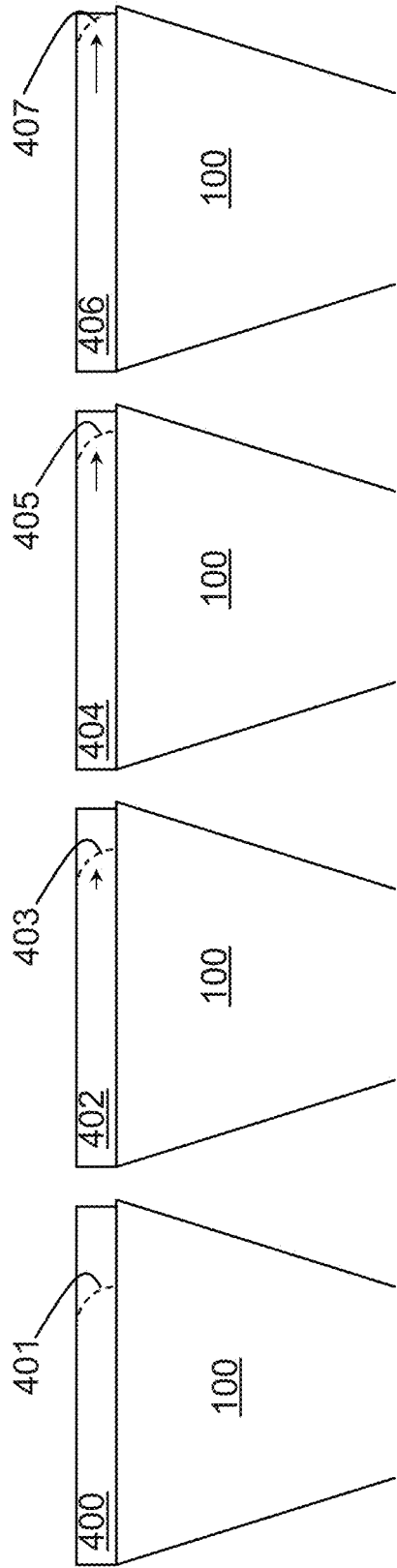
FIG. 14. illustrates a side (sagittal) view of a set of tibial inserts according to some embodiments of the present invention.

FIG. 14. illustrates a side (sagittal) view of a set of tibial inserts according to some embodiments. A set of tibial inserts (400,402,404,406) is provided, each insert comprising a posterior wall (401,403,405,407, respectively) that is located in a different position along an anterior-posterior axis. By shifting the posterior walls (401,403,405,407) in a posterior direction, tension within a preserved PCL can be increased independently of the size, thickness, and/or articular configuration of the inserts (400,402,404,406).

Figure 15:
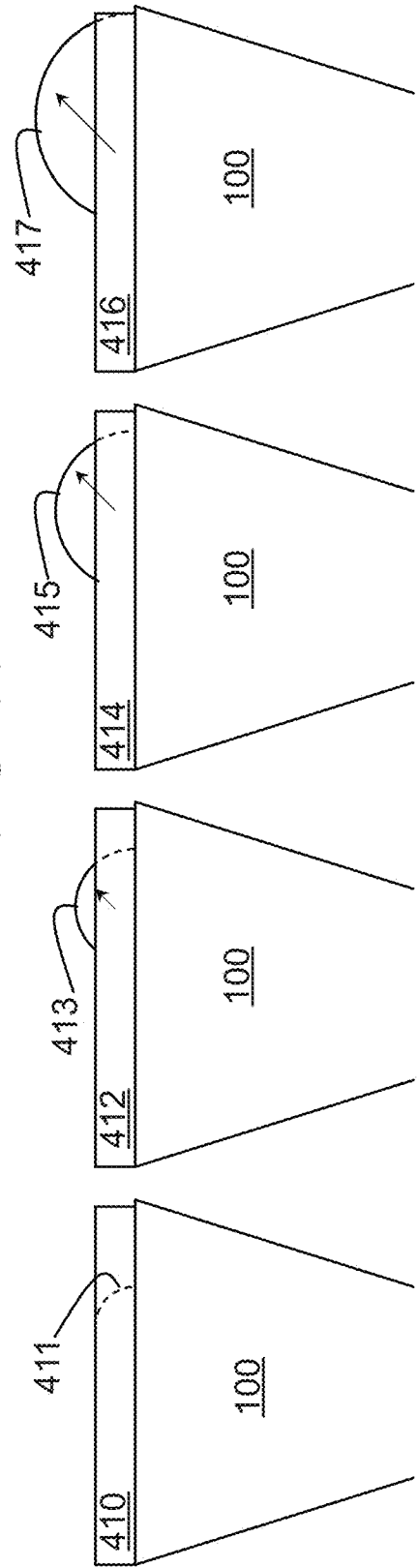
FIG. 15. illustrates a side (sagittal) view of a set of tibial inserts according to some embodiments.
Figure 16:
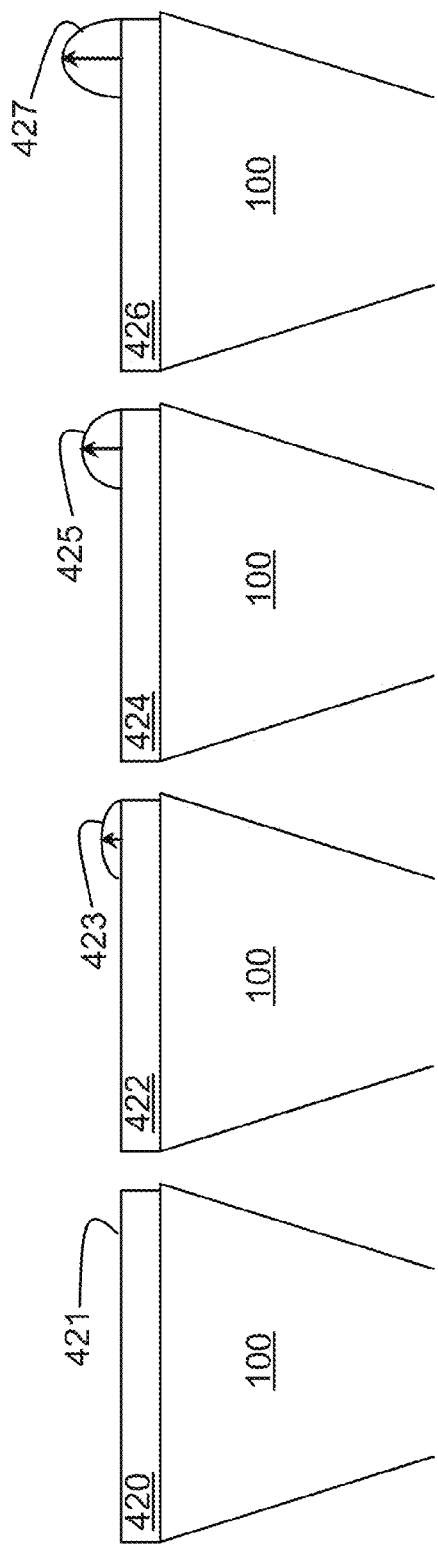
FIG. 16. illustrates a side (sagittal) view of a set of tibial inserts according to some embodiments.
Figure 17:
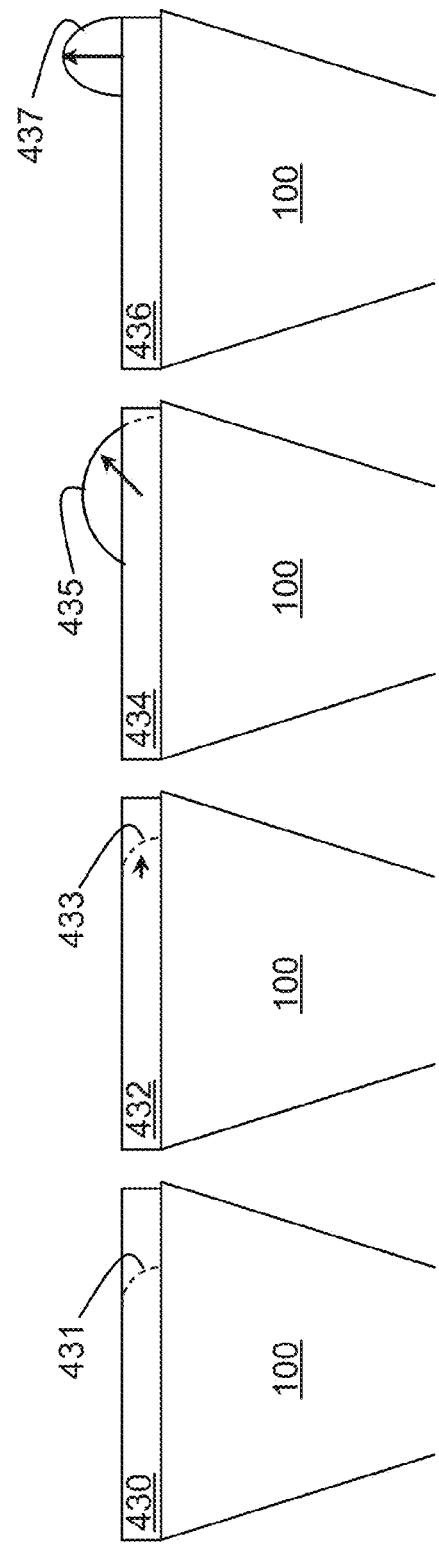
FIG. 17. illustrates a side (sagittal) view of a set of tibial inserts according to some embodiments.

While FIGS. 3-14 show embodiments utilizing geometry changes within a transverse plane to tension in the PCL and/or change direction of forces imparted by and acting on the PCL, FIGS. 14-16 illustrate how tensions and force directions associated with the PCL may be changed by utilizing geometry changes in a sagittal plane as well. FIG. 17 illustrates how tensions and force directions associated with the PCL may be changed by utilizing geometry changes in both transverse and sagittal planes. One of ordinary skill in the art may appreciate that complex three-dimensional surfaces in all dimensions and planes (transverse, sagittal, and coronal) may be envisaged from the disclosure of this specification. FEA testing may be advantageously utilized with advanced programs, such as LifeMOD or KneeSIM, to develop an ideal or optimized shape for the PCL-tensioning means disclosed herein. LifeMOD and KneeSIM are trademarks of LifeModeler, Inc., 2730 Camino Capistrano, Suite 7, San Clemente, Calif.

FIG. 15 illustrates a side (sagittal) view of a set of tibial inserts according to some embodiments. A set of tibial inserts (410,412,414,416) is provided, each insert comprising a posterior wall geometry (411,413,415,417, respectively) which is located in a different position along an anterior-posterior axis. By shifting the posterior walls (411,413,415,417) more posteriorly as well as superiorly, tension within a preserved PCL can be increased independently of the size, thickness, and/or articular configuration of the inserts (410,412,414, 416).

FIG. 16 illustrates a side (sagittal) view of a set of tibial inserts according to some embodiments. A set of tibial inserts (420,422,424,426) is provided, each insert comprising a posterior wall geometry (421,423,425,427, respectively) that is located in the same position relative along an anterior-posterior axis. By shifting the posterior walls (421,423,425,427) more superiorly, tension within a preserved PCL can be increased independently of the size, thickness, and/or articular configuration of the inserts (420,422,424,426).

FIG. 17 illustrates a side (sagittal) view of a set of tibial inserts according to some embodiments. A set of tibial inserts (430,432,434,436) is provided, each insert comprising a posterior wall geometry (431,433,435,437, respectively) that is located in the same position relative along an anterior-posterior axis. By shifting the posterior walls (431,433,435,437) purely posteriorly, posteriorly and superiorly, purely superiorly and various combinations thereof, tension within a preserved PCL can be increased independently of the size, thickness, and/or articular configuration of the inserts (430,432, 434,436).

Figure 18:
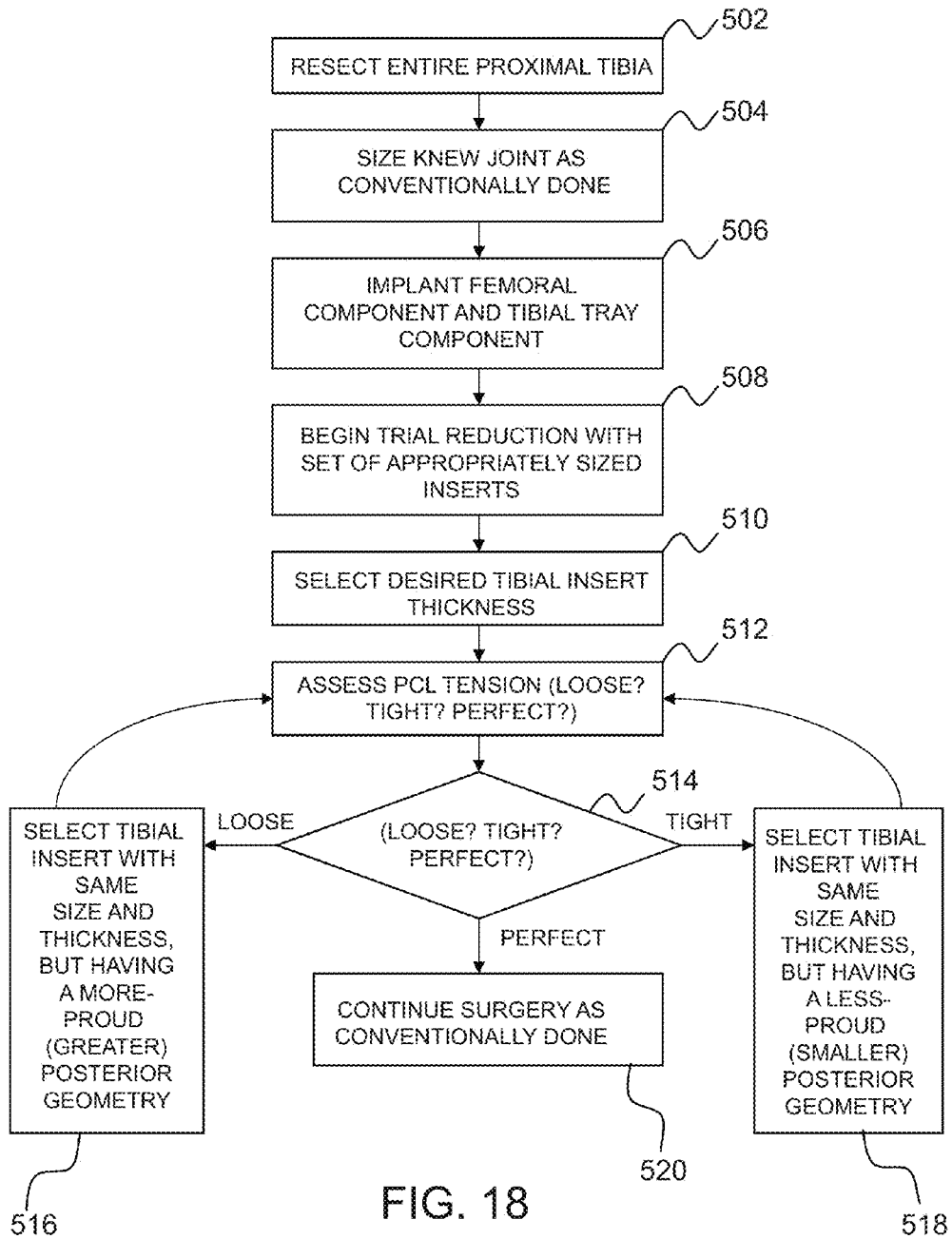
FIG. 18. illustrates a method of using a system according to some embodiments.

FIG. 18. is a schematic flowchart illustrating a method of using a system according to some embodiments. First, the entire proximal tibia is resected (502). The knee is then sized as conventionally done (504). Femoral and tibial tray implantation (506) is then performed. Step (506) may not be required for hemi-arthroplasty cases or for procedures utilizing cemented tibial inserts that do not use conventional tibial trays. Next, trial reductions are performed using a series of correctly-sized tibial inserts (508). Trial reduction may include a full range of motion assessment, drawer test, etc. After a desired tibial insert thickness is selected (510), the surgeon assesses the posterior-cruciate ligament for proper tensioning and function (512). If the prosthesis performs well, the surgeon may finish surgery in a conventional manner (520). If the PCL is too loose, the surgeon may try another insert having the same thickness and size with the exception of a greater or more "proud" posterior geometry to stretch and tighten the PCL as shown in step (516). Alternatively, if the PCL is too tight, the surgeon may try another insert having the same thickness and size with the exception of a smaller or less "proud" posterior geometry to loosen the PCL as shown in step (518). In addition to steps (514),(516), and (518), the surgeon may select other tibial insert options which change the angle, position in space, or location of the PCL independently or in combination with the steps of adjusting tension (step not illustrated).

Figure 19A:
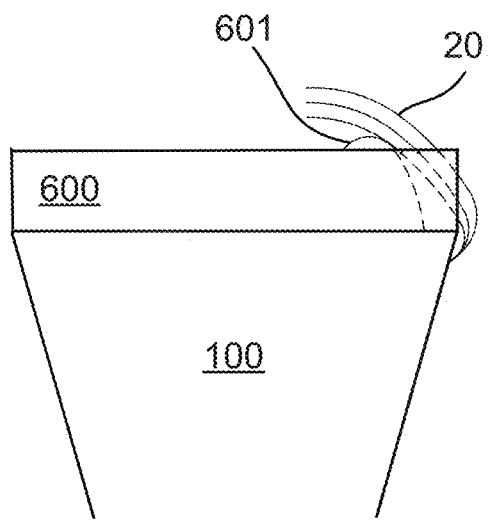
FIGS. 19A and 19B schematically illustrate a proximal tibia after a PCL sparing resection and tibial inserts positioned thereon according to some embodiments.
Figure 19B:
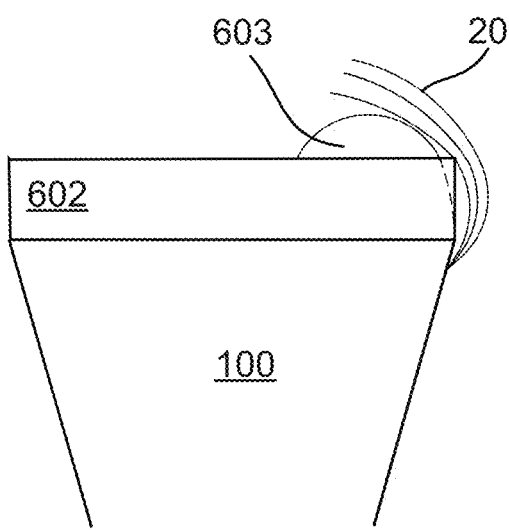

FIGS. 19A and 19B schematically illustrate a proximal tibia (100) after a PCL sparing resection and tibial inserts (600, 602) positioned thereon according to some embodiments. As schematically illustrated by these Figures, the different posterior wall geometries (601, 603) of the two inserts (600, 602) interact differently with the PCL (20). For instance, the posterior wall geometry (601) of FIG. 19A allows the PCL (20) to extend in a relatively straight line between its tibial attachment point and its attachment point on the distal femur (not shown). Conversely, the posterior wall geometry (603) of FIG. 19B forces the PCL (20) to wrap about it to a greater extent. Accordingly, the PCL (20) is more curved when positioned with respect to the insert (602) of FIG. 19B, and would likely be tensioned to a greater extent.

Alternative embodiments may include various mechanisms for adjusting PCL tension comprising geometries for optimizing PCL function, geometries for controlling the medial-lateral position of the PCL, geometries for controlling the height of the PCL relative to a surface of the tibial insert, geometries for changing or controlling the angle of the PCL relative to a surface of the tibial insert as viewed in the sagittal plane, geometries for changing or controlling the angle of the PCL relative to a surface of the tibial insert as viewed in a transverse plane along the superior-inferior axis, geometries for controlling the internal-external rotation of the PCL relative to a surface of the tibial insert, geometries for controlling the convexity or concavity of the surface and to reduce sliding of the PCL within a transverse plane, and other geometries without limitation. At least some embodiments of the invention also may be advantageously utilized with other surgical procedures requiring soft tissue balancing or release after bone cuts have been made or procedures which might involve soft tissues coming in contact with an orthopaedic implant or prosthesis. The shapes, geometries, and configurations included in this disclosure may further comprise surface treatments to optimize frictional and biological interactions between the means for PCL tensioning and the PCL or other surrounding soft-tissues. Such surface treatments may include without limitation, material surface treatments (e.g., metallurgical, ceramic-based, and/or polymeric surface treatments such as selective cross-linking) or additive surface treatments (e.g., antioxidants, antimicrobial/anti-infection, and pain management additives). The means for tensioning the PCL as described herein may be comprised of a material dissimilar to the material of the tibial insert.

In some instances, such as for bi-cruciate retaining prostheses, it may be desirable to adjust tension in the ACL alone, or in combination with tensioning the PCL. Therefore, while mechanisms for tensioning the PCL has been disclosed in greater detail in this specification, similar mechanisms for tensioning a preserved ACL may be equally-employed on a middle or anterior portion of a tibial insert in a similar fashion, in order to adjust tension in the ACL as well as PCL. ACL tensioning mechanisms (if provided) may be adapted to work in combination with, or independently of PCL tensioning.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments.

We claim:

1. A method of changing tension in the posterior cruciate ligament (PCL) during total knee arthroplasty, the method comprising:
   (a) determining a desired size for a knee implant for the knee joint;
   (b) implanting a tibial tray component to a resected tibial surface;
   (c) selecting at least one series of knee arthroplasty components of the desired size relative to the joint, the at least one series including at least a first trial tibial insert and a second trial tibial insert, wherein the first and second trial tibial inserts are of equal size and of equal thickness;
   (d) coupling the first trial tibial insert to the tibial tray component such that the posterior cruciate ligament is in wrapping contact with a first wrapping surface of the first trial tibial insert;
   (e) assessing PCL tension while the posterior cruciate ligament is in wrapping contact with the first wrapping surface;
   (f) coupling the second trial tibial insert to the tibial tray component such that the posterior cruciate ligament is in wrapping contact with a second wrapping surface of the second trial tibial insert;
   (g) assessing PCL tension while the posterior cruciate ligament is in wrapping contact with the second wrapping surface; and
   (h) implanting a final knee joint implant in the joint,
   wherein each of the first and second wrapping surfaces are notches formed proximate posterior edges of the first and second trial tibial inserts, said notches are centrally located between medial and lateral condylar articulating surfaces;
   wherein each of the first and second trial tibial inserts include an anterior-posterior axis and wherein the first wrapping surface of the first trial tibial insert is positioned further posteriorily along the anterior-posterior axis of the first trial tibial insert relative to the second wrapping surface of the second trial tibial insert, and wherein the first wrapping surface of the first trial tibial insert extends further superiorly relative to the second wrapping surface of the second trial tibial insert; and
   wherein a geometry of the first wrapping surface of the first trial tibial insert is different from a geometry of the second wrapping surface of the second trial tibial insert such that the first wrapping surface of the first trial tibial insert is configured to generate at least one of a different tension in or direction of force on the posterior cruciate ligament relative to the second wrapping surface of the second trial tibial insert.

* * * * *